United States Patent
Dooney, Jr.

(10) Patent No.: US 12,011,162 B2
(45) Date of Patent: Jun. 18, 2024

(54) SUTURE RELEASE CONSTRUCTS AND METHODS OF TISSUE FIXATION

(71) Applicant: Arthrex, Inc., Naples, FL (US)

(72) Inventor: Thomas Dooney, Jr., Naples, FL (US)

(73) Assignee: Arthrex, Inc., Naples, FL (US)

(*) Notice: Subject to any disclaimer, the term of this patent is extended or adjusted under 35 U.S.C. 154(b) by 163 days.

(21) Appl. No.: 17/516,124

(22) Filed: Nov. 1, 2021

(65) Prior Publication Data
US 2023/0139434 A1    May 4, 2023

(51) Int. Cl.
*A61B 17/06*    (2006.01)
*A61B 17/04*    (2006.01)

(52) U.S. Cl.
CPC .... *A61B 17/06166* (2013.01); *A61B 17/0401* (2013.01); *A61B 2017/0495* (2013.01)

(58) Field of Classification Search
CPC .......... A61F 2/0811; A61F 2002/0852; A61B 17/0401; A61B 17/06; A61B 2017/06052; A61B 17/06166; A61B 2017/06171; A61B 2017/06176; A61B 2017/0618; A61B 2017/06185; A61B 2017/0619; A61B 17/0466; A61B 17/0469; A61B 90/92; A61B 2017/0475; A61B 2017/0477
See application file for complete search history.

(56) References Cited

U.S. PATENT DOCUMENTS

| | | |
|---|---|---|
| 7,857,830 B2 | 12/2010 | Stone et al. |
| 7,905,903 B2 | 3/2011 | Stone et al. |
| 8,562,645 B2 | 10/2013 | Stone et al. |
| 9,381,013 B2 | 7/2016 | Norton |
| 9,795,373 B2 | 10/2017 | Sengun |
| 11,413,031 B2* | 8/2022 | Astorino .......... A61B 17/06166 |
| 2008/0027446 A1* | 1/2008 | Stone ................. A61B 17/0482 606/151 |
| 2018/0221010 A1* | 8/2018 | Lund ................. A61B 17/0401 |
| 2018/0221133 A1* | 8/2018 | Lund ................. A61B 17/0401 |
| 2020/0214691 A1* | 7/2020 | Astorino ........... A61B 17/0482 |
| 2021/0113204 A1 | 4/2021 | Walters et al. |
| 2021/0244401 A1 | 8/2021 | Burkhart et al. |

FOREIGN PATENT DOCUMENTS

| | | | | |
|---|---|---|---|---|
| GB | 2575657 A | * | 1/2020 | ......... A61B 17/0467 |
| WO | WO-2012096707 A1 | * | 7/2012 | ....... A61B 17/00234 |

* cited by examiner

*Primary Examiner* — Katherine M Shi
(74) *Attorney, Agent, or Firm* — Potomac Law Group, PLLC

(57) ABSTRACT

Reinforced surgical constructs and methods of tissue repairs. A surgical construct can offer both repair and shuttling capabilities to allow for a single pass to load multiple sutures at once. A surgical construct includes one or more repair sutures provided with one or more junctions (one or more releasable stitches), to allow the repair sutures to be joined and subsequently released. At least one of the one or more junctions (releasable stitches) can be formed by weaving back and forth another flexible strand (releasing suture) through the one or more repair sutures. When the flexible strand is pulled, it pulls out the one or more junctions (releasable stitches) from the repair sutures, freeing the repair sutures. The surgical construct may be part of a knotless or knotted construct.

18 Claims, 2 Drawing Sheets

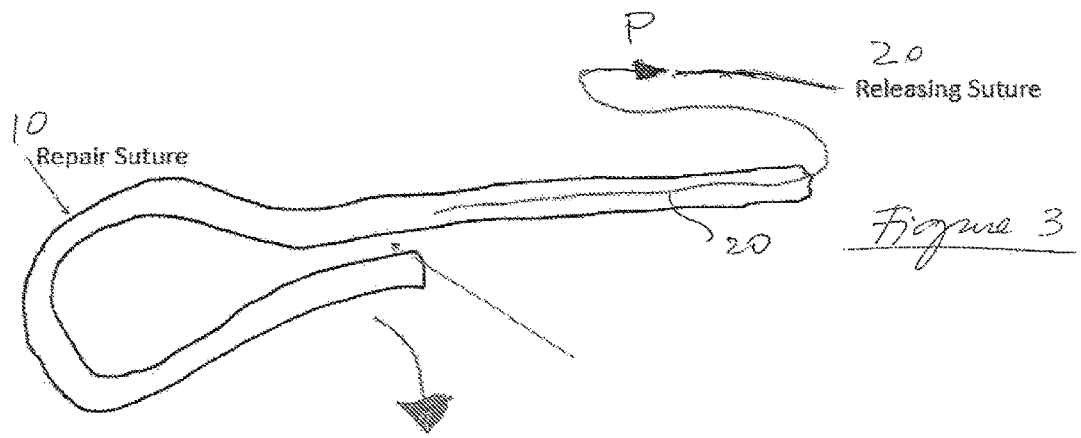
Figure 3
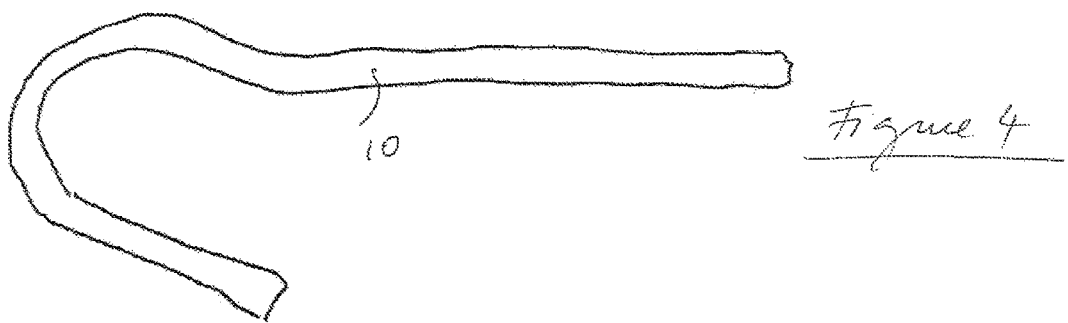
Figure 4
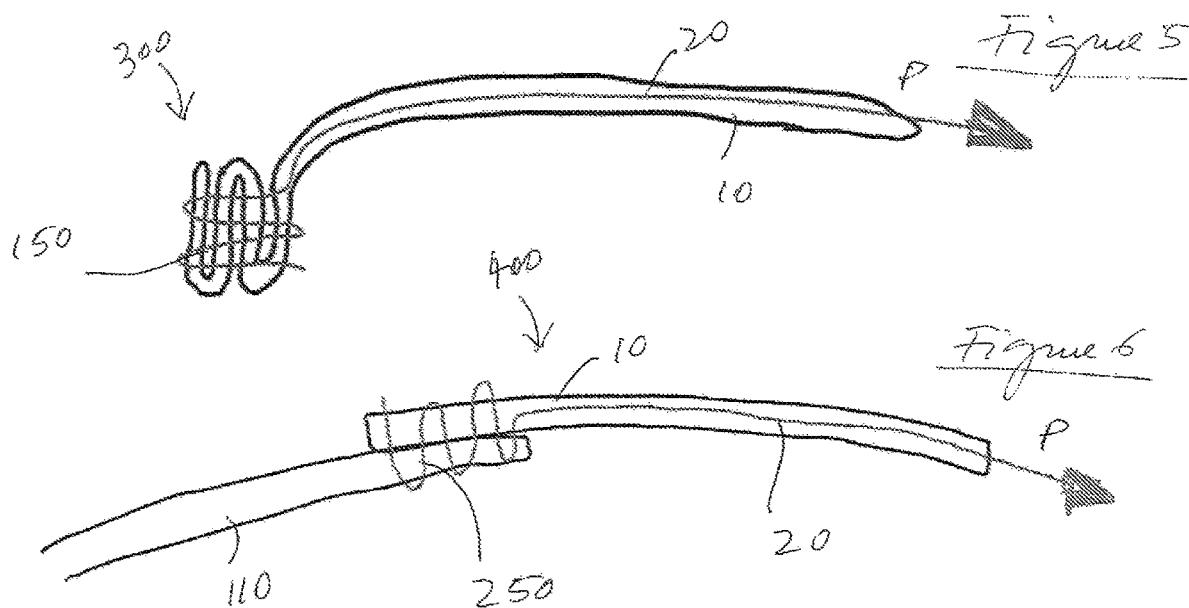
Figure 5
Figure 6

SUTURE RELEASE CONSTRUCTS AND METHODS OF TISSUE FIXATION

BACKGROUND

The disclosure relates to surgical devices and, more specifically, to sutures and associated methods of tissue repairs.

SUMMARY

Surgical constructs with releasable junctions and methods of tissue repairs are disclosed. A surgical construct can offer both repair and reinforcement capability. A surgical construct can include one or more repair strands provided with one or more releasable junctions (one or more releasable stitches), to allow the repair strands to be joined and subsequently released. At least one of the one or more releasable junctions (releasable stitches) can be formed by passing back and forth another flexible strand (releasing suture) through the one or more repair strands to form a plurality of passes. When the another flexible strand is pulled, it pulls out the one or more releasable junctions (releasable stitches) from the repair strands, releasing the repair strands. The surgical construct may be part of a knotless or knotted construct.

Methods of forming a releasable, stitched junction capable of being released to allow repair strands to be disengaged/disjoined are also provided. One or more repair strands are provided with at least one or more releasable junctions (one or more releasable stitches) formed by another independent strand (releasing suture) which is passed/shuttled through the one or more repair strands, to form a releasable junction. The another independent strand (releasing suture) may be similar to or different from the one or more repair strands, and may have similar or different characteristics and properties as those of the repair strands. The one or more releasable junctions (releasable stitches) can be removed to allow release of the repair strands by pulling on the releasing suture.

Methods of tissue repair are also disclosed. A first tissue is approximated to a second tissue with a repair strand provided with at least one or more releasable junctions (one or more releasable stitches) formed by a releasing suture that is passed or weaved back and forth through at least a portion of the repair strand. When the releasing suture is pulled, it pulls out the releasable stitch from the repair suture, freeing up the repair suture. The releasable junction provides additional support, strength, and reinforcement of the tissue repair. In an embodiment, a repair strand with at least one releasable junction (releasable stitch) is attached to a first tissue and to a second tissue, to provide a reinforced tissue repair and assist in surgical procedures requiring repair sutures to be joined to each other, as well as released from each other at a certain time during the surgery.

BRIEF DESCRIPTION OF THE DRAWINGS

FIGS. 3 and 4 illustrate subsequent steps of removing the releasable stitch of the construct of FIG. 1.

FIG. 5 illustrates a surgical construct according to another exemplary embodiment.

FIG. 6 illustrates a surgical construct according to another exemplary embodiment.

DETAILED DESCRIPTION

Figure 1:
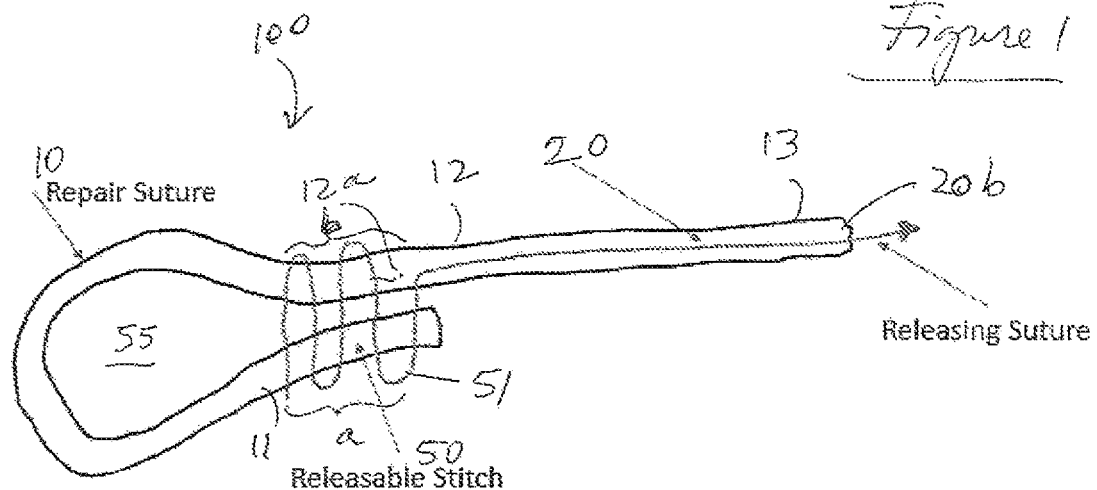
FIG. 1 illustrates a surgical construct according to an exemplary embodiment.

The disclosure provides surgical constructs formed of flexible strands that are joined together and subsequently disengaged. The surgical constructs are suturing constructs.

The surgical constructs include a repair strand (flexible strand such as suture) provided with at least one releasable stitch formed by a releasing suture (another flexible strand such as suture) that is passed or weaved back and forth through at least a portion of the body of the repair strand to form a releasable stitch. When the releasing suture is pulled, the releasable stitch is removed (pulled out) from the repair strand.

The surgical constructs can be employed for passing or shuttling at least one length of flexible material, for example suture such as high strength suture, tape, wire, cable, or fabric. After the passing or shuttling of various lengths of flexible materials with the surgical constructs in a first configuration (having the releasable stitch), the surgical constructs can attain a second configuration different from the first configuration (without the releasable stitch). The surgical constructs may be knotless or knotted. The surgical constructs may be part of additional knotless or knotted construct(s) and/or may be employed in conjunction with knotless or knotted construct(s).

The surgical constructs permit passing and secure attachment of additional flexible strands through and with the repair strand, with increased strength and reinforcement capabilities. The ability to pass additional sutures through and with the repair strand would permit multiple suture strands to be loaded at a tissue repair site without the requirement of individually passing the suture through the tissue more than once. Surgical repairs with improved strands having reinforced junctions/suture releasable stitches such as the improved strands of the present disclosure (and as detailed below) provide multiple strands joined at a releasable junction point which provides increased strength and supporting capabilities at a repair site, with the benefit of releasing the repair strands as desired during the surgical procedure.

The surgical constructs include a repair strand that is joined into a predetermined configuration or bounded with other repair strands together by a releasing suture. The releasing suture forms a releasable stitch. The surgical constructs provide for improved methods of tissue repair and multiple suture strand loading techniques with a single suture needle passage.

The surgical construct in the predetermined configuration can be employed as a passing/shuttling loop, through which the same suture strand and/or another independent strands (sutures) may be passed in a single pass step, for improved tissue repair constructs. The surgical construct provides a site where additional sutures or strands or flexible materials may be passed/threaded through loops formed by the releasable stitch. The repair strands can be disengaged by pulling on the releasing suture to remove the releasable stitch and release the repair strands.

Referring now to the drawings, where like elements are designated by like reference numerals, FIGS. 1-6 illustrate various views of surgical constructs 100, 200, 300, 400 (suture releasable stitch constructs 100, 200, 300, 400; suturing constructs 100, 200, 300, 400; constructs 100, 200, 300, 400; assemblies 100, 200, 300, 400) of the present disclosure.

FIG. 1 depicts construct 100 with repair suture 10 (repair strand 10; first flexible strand 10; strand 10; flexible member 10) which may be formed of suture or any similar material and releasing suture 20 (releasing strand 20; second flexible strand 20; strand 20; flexible member 20), connected by releasable stitch 50 (stitch 50; interconnection 50; junction 50; releasable junction 50; suture releasable stitch 50; release stitch 50; connecting region 50).

Repair suture 10 of FIG. 1 can include a middle region 12 with two tail regions 11, 13 (tails 11, 13; ends 11, 13) and one exemplary releasing suture 20 being provided extending through the middle region 12 and along a longitudinal axis 12a of the middle region 12 and out of tail 13. The middle region 12 can be a suture or tape, for example a round suture or flat suture tape. The middle region can have a constant diameter/dimensions or a gradual taper. The two tail regions 11, 13 can be formed of round suture, with same or different diameter.

Middle region 12 can have cross-sections of various forms and geometries, including round, elliptical, rectangular or flat, among others, or combination of such forms and geometries. In an exemplary embodiment only, middle region 12 can be provided as a braided round suture that can be coreless. The diameter of middle region 12 may be constant or may vary. The middle region 12 can be any suture strand or suture tape, for example, Arthrex FiberWire® suture (disclosed in U.S. Pat. No. 6,716,234, the entire disclosure of which is incorporated herein by reference). However, the surgical constructs 100, 200, 300, 400 can be used with any type of flexible material or suture known in the art. The tail regions 11, 13 may have similar or different diameters and/or widths. As illustrated in FIG. 1, each of the widths/diameters of the tail regions 11, 13 is about similar to the width/diameter of the middle region 12. Tail regions 11, 13 may have similar or different lengths. One or both of the tail regions 11, 13 may have a very fine end that is coated, impregnated, or stiffened with a material such as plastic, for example. One or both of the tail regions 11, 13 may include a tapered end that terminated in a very fine end.

For simplicity, FIGS. 1-6 illustrate repair suture 10 with only one exemplary releasable stitch 50; however, the disclosure contemplates strands and flexible materials with any number of releasable stitches 50, depending on the desired number of working strands and the particulars of each surgical repair. In addition, any number of repair sutures 10 may be employed with any number of releasing sutures 20 and releasable stitches 50.

Releasable stitch 50 may be formed by passing releasing suture 20 at least once, preferably multiple times, through at least two separate regions/portions of the repair suture 10, as shown in FIG. 1, for example. Releasing suture 20 is provided inside the repair suture 10, by for example, being fed inside the repair suture 10. Releasable stitch 50 can be formed by passing back and forth the releasing suture 20 at different, spaced location and through bodies of portions/lengths/regions a, b of the repair suture 10. Releasable stitch 50 can include a plurality of passes 51 (for example, five passes 51, as illustrated in FIG. 1) but it must be understood that the disclosure contemplates releasable stitch 50 with any number of passes 51 formed through the repair suture 10. Additional passes through the repair suture 10 would typically provide a stronger overall stitch 50.

FIG. 1 shows an "inside releasing suture" embodiment, i.e., releasing suture 20 is being fed inside of the repair suture 10 with the releasing suture 20 exiting an open end of the repair suture 20, for example, a most distal end 20b. The releasable stitch is provided adjacent tail 11 to form continuous, uninterrupted, flexible, knotless loop 55. The "inside releasing suture" embodiment confers a clean appearance to the overall construct 100 and it is easier to manage. The repair suture 10 is in a first configuration (a "loop configuration").

The releasable stitch 50 is formed of plurality of passes 51 by sewing back-and-forth strand 20 through the repair suture 10. The more passes through the repair suture the stronger the overall stitch becomes. At least one of the plurality of passes 51 is provided within the body and end tail/region 11 of the repair suture 10 and along the lengths a, b of the repair suture 10 to permit for the passing/shuttling of the same repair suture 10 and/or other additional repair strands (flexible strands or similar elements such as suture, suture tapes, etc.) through the loop 55. This aspect allows for additional sutures or tapes or any flexible material to pass through the reinforced loop to increase the strength of the repair.

One or more stitches 50 may be provided extending through and along the body of regions a and b of repair suture 10, to attach/join/connect the regions a and b together, in a secured yet non-permanent manner, and to form a suture loop 55 (flexible, closed loop with a fixed perimeter). The suture loop 55 can allow passing of another strand(s) through the loop to aid in various tissue repairs. If multiple releasable stitches 50 are employed, the releasable stitches may have similar or different geometries and shapes and may be formed by similar or different releasing sutures.

Releasable stitch 50 can be formed by passing/sewing/weaving the releasing suture 20 through repair strand 10 at different locations and in at least two different directions, a first, longitudinal direction A about parallel to longitudinal axis 12a of repair suture 10 and a second direction B about orthogonal to longitudinal axis 12a of repair suture 10. Releasing suture 20 may be any flexible strand, for example, suture strands, suture tapes, nitinol strands, FiberWire® suture, TigerWire® suture, or FiberLink™ among many others. One or more releasing sutures 20 may pass through repair suture 10. When the releasing suture 20 is pulled, it pulls out the releasable stitch 50 from the repair suture 10 and opens up the loop 55.

Figure 2:
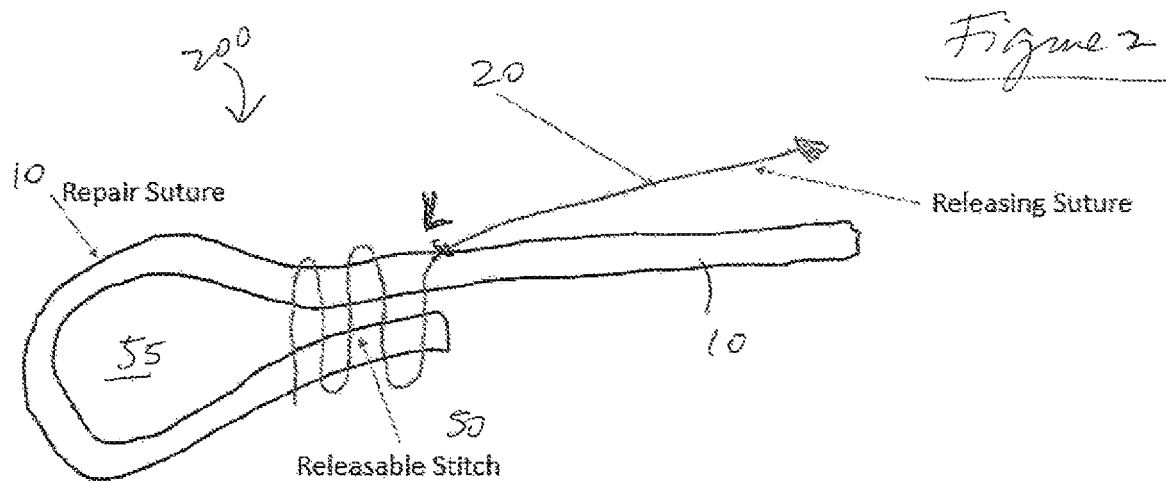
FIG. 2 illustrates a surgical construct according to another exemplary embodiment.

FIG. 2 illustrates surgical construct 200 which is similar in part to construct 100 detailed above (the "inside releasing suture" embodiment with a releasable suture loop) but differs in that construct 200 includes releasing suture 20 (a separate, independent strand 20) which exits the repair suture 10 at a location "L" situated along the middle region 12 or tail 13, and not at a most distal end 20b of the tail 13, as in the first embodiment. The embodiment of FIG. 2 is an "outside releasing suture" construct with a releasable suture loop, wherein the releasing suture 20 is fed outside of the repair suture 10. Depending on how the stitch 50 is used and upon the complexity of the surgical activity, the releasing suture 20 may provide additional benefits if fed outside the repair suture.

FIGS. 3 and 4 illustrate subsequent steps of removing the releasable stitch 50 of exemplary construct 100 of FIG. 1. Pulling on the releasing suture 20 in direction "P" along the length of suture 20 and away from the repair suture 10, allows the releasing suture 20 to remove the releasable stitch 50 and to confer the repair suture 10 a second configuration. The repair suture loop 55 is free to open. FIG. 4 illustrates repair suture 10 in the second configuration (non-loop configuration), with releasing suture 20 completely removed and loop 55 completely opened (no loop).

FIG. 5 illustrates surgical construct 300 which is similar in part to constructs 100, 200 detailed above, but differs in that construct 300 includes releasing suture 20 which extends longitudinally through the middle region 12 or one of the tails 11, 13 and the other one of the tails 11, 13 of the repair suture 10, i.e., without a loop formation. Releasing suture 20 also passes through a plurality of regions of the repair suture 10 (for example, four or more separate regions, as shown in FIG. 5) to form releasable stitch 150 in the form of a releasable suture bunch/knot. When releasing suture 20 is pulled in direction "P" to pull out of the repair suture 10, the stitch 150 is removed and the repair suture 10 becomes unbunched/unknotted, i.e., repair suture 10 changes from first to second configuration to become a flexible, free strand without any joined or connected sections.

FIG. 6 illustrates surgical construct 400 which is similar in part to constructs 100, 200, 300 detailed above, but differs in that construct 400 includes releasing suture 20 which forms releasable stitch 250 joining two or more repair sutures 10, 110 and extending longitudinally only through one of the repair sutures 10, 110, without a loop formation. When the releasing suture 20 is pulled, it pulls out the releasable stitch 250 from the repair sutures 10, 110 and frees the repair sutures 10, 110 (a "releasable sutures" embodiment).

Typically, sutures can be spliced (fixed spliced sutures) or tied together or joined permanently in different manners but they cannot be disengaged (set free subsequent to the splicing or joining other than being cut to open the joined region). The present disclosure provides a solution to join a suture in a predetermined configuration or to bind multiple sutures together, while also providing a simple method to release these sutures. The formed loop can be released by removing/uncoupling the suture release stitch from the repair suture of the surgical construct. After the stitch has been removed, the suture(s) attains and returns to the initial form/state.

A surgical construct 100, 200, 300, 400 includes one or more repair sutures 10, 110 provided with one or more junctions 50, 150, 250 (one or more releasable stitches 50, 150, 250), to allow the repair sutures 10, 110 to be joined and subsequently released. At least one of the one or more junctions 50, 150, 250 (releasable stitches) can be formed by passing or weaving back and forth another flexible strand 20 (releasing suture 20) through the one or more repair strands 10, 110. When the releasing suture 20 is pulled, it pulls out the one or more junctions 50, 150, 250 (one or more releasable stitches 50, 150, 250) from the repair sutures 10, 110, releasing the repair sutures 10, 110 and opening up loop 55. The surgical construct 100, 200, 300, 400 may be a knotless or knotted construct, or may be part of a knotless or knotted construct.

Methods of forming a reinforced or stitched junction 50, 150, 250 (one or more releasable stitches 50, 150, 250) capable of being released to allow repair strands to be disengaged/disjoined are also provided. One or more repair sutures 10, 110 are provided with at least one or more junctions 50, 150, 250 (one or more releasable stitches 50, 150, 250) formed by another independent strand 20 (releasing suture 20) which is passed/shuttled through the one or more repair sutures 10, 110, to form a junction. The another independent strand (releasing suture) may be similar to or different from the one or more repair sutures, and may have similar or different characteristics and properties as those of the repair strands. The one or more junctions 50, 150, 250 (one or more releasable stitches 50, 150, 250) can be removed to allow release of the repair strands by pulling on the releasing suture.

Methods of tissue repair are also disclosed. A first tissue is approximated to a second tissue with a repair suture 10, 110 provided with at least one or more junctions 50, 150, 250 (one or more releasable stitches 50, 150, 250) formed by a releasing suture 20 that is passed back and forth through at least two different locations of the repair suture 10, 110. When the releasing suture 20 is pulled, it pulls out the releasable stitch 50, 150, 250 from the repair suture 10, 110, freeing up the repair suture 10, 110. The junction 50, 150, 250 (one or more releasable stitches 50, 150, 250) provides additional support, strength, and reinforcement of the tissue repair as well as of the repair suture 10, 110. In an embodiment, a repair suture 10, 110 with at least one reinforced junction 50, 150, 250 (one or more releasable stitches 50, 150, 250) is attached to a first tissue and to a second tissue, to provide a reinforced tissue repair and assist in multiple surgical procedure requiring repair sutures to be joined to each other, as well as released from each other to go back to their initial shape/configuration/state.

A repair suture 10, 110 includes a releasable stitch 50, 150, 250. The releasable stitch 50, 150, 250 includes a plurality of passes 51 formed by passing at least another strand 20 multiple times through two regions a, b of the repair suture 10, 110. When the another strand 20 is pulled out of the suture 10, 110, the releasable stitch 50, 150, 250 is removed from the repair suture.

A surgical construct 100, 200, 300, 400 comprises a repair suture 10, 110 with at least one releasable stitch 50, 150, 250 formed of a plurality of passes 51 which extend in between two separate regions a, b of the repair suture 10, 110 and which are formed by a strand 20 passing back and forth through the two separate regions a, b of the repair suture 10, 110 to form the releasable stitch 50, 150, 250. The strand 20 is passed at an angle relative to a longitudinal axis 12a of the repair suture 10, 110 to connect the two separate regions a, b or the two separate repair sutures 10, 110 and form a loop 55. The repair suture 10, 110 has a middle region 12 and two tail regions 11, 13 adjacent the middle region 12. The releasable stitch 50, 150, 250 is removable when the strand 20 is pulled out of the repair suture 10, 110.

A surgical construct 100, 200, 300, 400 comprises a suture 10, 110 with a middle region 12 and two end tails 11, 13; and a strand 20 passed multiple times through the middle region 12 and through one of the end tails 11, 13 to form a closed, flexible, continuous end loop 55 with a fixed perimeter and a releasable junction 50, 150, 250, and to connect the one end of the tails 11, 13 to the middle region 12. The strand 20 passes through other of the two end tails 11, 23.

A method of suturing comprises (i) passing a suture construct 100, 200, 300, 400 through or around tissue, the suture construct comprising a first flexible strand 10, 110 with a closed, flexible, continuous end loop 55 with a fixed perimeter and a releasable stitch 50, 150, 250, and a second flexible strand 20 passed through and in between at least two separate longitudinal lengths a, b of the first flexible strand 10, 110 to form the releasable stitch 50, 150, 250 and the closed, flexible, continuous end loop 55 with a fixed perimeter; and (ii) pulling on the second flexible strand 20 to remove the releasable stitch 50, 150, 250 and to open the closed, flexible, continuous end loop 55 with a fixed perimeter. The method further comprises threading at least another flexible strand through the closed, flexible, continuous end loop 55 with a fixed perimeter; and passing the another flexible strand through or around tissue together with the suture construct 100, 200, 300, 400. The first flexible strand 10, 110, the second flexible strand 20, and the another flexible strand can be passed simultaneously through the tissue, in a single pass step. The suture construct 100, 200, 300, 400 (with or without any additional strands) can be attached to a fixation device. The fixation device can be knotless or knotted. A knotless fixation device can be a swivel anchor or a pushlock anchor.

The surgical construct 100, 200, 300, 400 can be a shuttling/suture passer. The surgical construct 100, 200, 300, 400 can be a repair suture. The surgical construct 100, 200, 300, 400 can be a suturing construct. The suture may be a round suture or a suture tape, or combination thereof. The suture may be high strength suture, tape, suture tape, combination of suture and tape, wire, cable, or fabric, among many others.

Methods of tissue repair are also disclosed. In an embodiment, additional flexible strands can be passed simultaneously with a suture construct 100, 200, 300, 400 by conducting a single pass through tissue to be repaired (ligament, tendon, graft, etc.). The suture construct (repair suture 10, 110 and releasing suture 20) and any additional flexible strands passed and secured through the loop 55 may be passed and/or shuttled simultaneously with or without a surgical instrument such as a suture passer. The suture construct and the additional flexible strands may be passed or shuttled simultaneously without loading a separate shuttling stitch or wire, and without passing each strand independently. One or more additional flexible strands may pass through one or more loops 55 (with a needle or a suture passer).

A method of tissue repair (for example, soft tissue to soft tissue, or soft tissue to bone fixation) includes passing a suturing construct 100, 200, 300, 400 through tissue and securing the tissue with the suturing construct. The suturing construct 100, 200, 300, 400 may be passed through or around tissue by loading the construct onto a suture passer and simultaneously passing a repair suture together with the releasing suture and any additional repair strands. Additional repair strands are passed through the closed loop 55 of the suturing construct and passed/shuttled through or around tissue without the need to pass each additional repair strand individually. A single pass loads multiple repair strands at once. The tissue repairs may employ at least one knotless and/or knotted fixation device. The knotless fixation devices may be knotless anchors, for example, swivel and/or screw-in suture anchors and/or push-in anchors (such as an Arthrex SwiveLock® anchor or a PushLock® Anchor). In an exemplary embodiment only, the fixation device is a knotless suture anchor such as the two-piece Arthrex PushLock® anchor, disclosed in U.S. Pat. No. 7,329,272, or an Arthrex SwiveLock® anchor, disclosed in U.S. Pat. No. 8,012,174 issued Sep. 6, 2011, and U.S. Pat. No. 9,005,246 issued Apr. 14, 2015, the disclosures of all of which are fully incorporated by reference in their entirety herein.

The surgical constructs 100, 200, 300, 400 described above may be formed of strands of a high strength suture material with surgically-useful qualities, including knot tie down characteristics and handling, such as Arthrex fiber-Wire® suture disclosed in U.S. Pat. No. 6,716,234 the entire disclosure of which is incorporated herein by reference. The surgical constructs may be formed of optional colored strands (preferably black) to assist surgeons in distinguishing between suture lengths with the trace and suture lengths without the trace.

Surgical constructs 100, 200, 300 may be preferably coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture or tape, knot security, pliability, handleability or abrasion resistance, for example.

Strands 10, 100, 20 may be made of any known suture construct, such as multifilament, braided, knitted, woven suture, or including fibers of ultrahigh molecular weight polyethylene (UHMWPE). Flexible strands 10, 110, 20 can consist of, or consist essentially of, suture. Flexible strands 10, 110, 20 can be formed of any suture, tape, weave, fabric, ribbon, textile, web, or mesh, or any combinations of these materials. Flexible strands 10, 110, 20 can be formed of a high strength suture material such as FiberWire® suture, sold by Arthrex, Inc. of Naples, Fla., and described in U.S. Pat. No. 6,716,234, the disclosure of which is incorporated by reference herein. FiberWire® suture is formed of an advanced, high-strength fiber material, namely ultrahigh molecular weight polyethylene (UHMWPE), sold under the tradenames Spectra® (Honeywell International Inc., Colonial Heights, Va.) and Dyneema® (DSM N.V., Heerlen, the Netherlands), braided with at least one other fiber, natural or synthetic, to form lengths of suture material. Flexible strands 10, 110, 20 can be braided or multi-filament suture such as FiberTape® suture tape (as disclosed in U.S. Pat. No. 7,892,256, the disclosure of which is incorporated in its entirety herewith) or collagen tape, or wide "tape like" material, or combinations thereof.

Flexible strands 10, 110, 20 can consist essentially of suture or suture material, or combination of suture and other materials such as long chain synthetic polymers like polyester and nylon, or materials such as PET, silk nylon or absorbable polymers, or coating materials (such as wax, silk, or silicone products), among many others. Flexible strands 10, 110, 20 can consist of strands with cross-sections of various forms and geometries, including round, oval, rectangular, or flat, among others, or combinations of such forms and geometries. In an embodiment, at least one of flexible strands 10, 110, 20 can be provided as a suture which is braided, knitted or woven.

Flexible strands 10, 110, 20 can be also formed of a stiff material, or combination of stiff and flexible materials, depending on the intended application. Flexible strands 10, 110, 20 can be also coated and/or provided in different colors. In an embodiment, parts (or all) of suturing construct 100, 200, 300, 400 can be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture and/or tape, pliability, handleability or abrasion resistance, for example.

Flexible strands 10, 110, 20 can be also provided with tinted tracing strands, or otherwise contrast visually with other parts of the construct, which remain a plain, solid color, or displays a different tracing pattern, for example. Various structural elements of surgical construct 100, 200, 300, 400 may be visually coded, making identification and handling of the suture legs simpler. Easy identification of suture in situ is advantageous in surgical procedures.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A repair suture having two free open ends for suturing and with a releasable stitch formed by a releasing suture, wherein the releasing suture is connected to the repair suture by the releasable stitch, wherein the releasing suture extends along a longitudinal axis of the repair suture and out one of the two free open ends, and wherein the releasing suture is configured to be pulled out of the one of the two free open ends of the repair suture to pull out the releasable stitch from the repair suture and to free up the repair suture and the releasing suture.

2. The repair suture of claim 1, wherein the releasable stitch includes a plurality of passes formed by passing the releasing suture multiple times through two regions of the repair suture.

3. The repair suture of claim 2, wherein when the releasing suture is pulled out the one of the two free open ends of the repair suture, the releasable stitch is removed from the repair suture.

4. The repair suture of claim 3, wherein the releasing suture is configured to be pulled completely out of the repair suture.

5. The repair suture of claim 2, wherein the releasing suture is passed at an angle relative to a longitudinal axis of the repair suture to form the releasable stitch.

6. The repair suture of claim 5, wherein the angle is about 90 degrees.

7. The repair suture of claim 2, wherein the repair suture is a round suture and the releasing suture is a suture or tape.

8. The repair suture of claim 1, wherein the repair suture is a round suture with a middle region and the two free open ends.

9. The repair suture of claim 8, wherein the releasable stitch is provided at the middle region and the other one of the two free open ends.

10. The repair suture of claim 9, wherein at least a length of the releasing suture extends within the middle region and along the longitudinal axis of the repair suture.

11. A surgical construct comprising:
a repair suture with at least one releasable stitch formed of a plurality of passes extending in between two separate regions of the repair suture; and
a releasing suture passed back and forth multiple times through the two separate regions of the repair suture to form the plurality of passes, wherein the releasing suture extends within a length of the repair suture and along a longitudinal axis of the repair suture, so that, when the releasing suture is pulled out of an open end of the repair suture, the at least one releasable stitch is pulled out from the repair suture and removed from the repair suture, and the repair suture is released.

12. The surgical construct of claim 11, wherein the releasing suture is passed at an angle relative to a longitudinal axis of the repair suture to connect the two separate regions and form a loop.

13. The surgical construct of claim 11, wherein the repair suture has a middle region and two tail regions adjacent the middle region, wherein one of the two tail regions is the open end.

14. The surgical construct of claim 11, wherein at least one of the repair suture, the releasing suture, and the releasable stitch is visually coded.

15. A surgical construct comprising:
a suture with a middle region and two end tails; and
a releasing suture passed multiple times through the middle region and through one of the two end tails to form a closed, flexible, continuous end loop with a fixed perimeter and a releasable junction, and to connect the one of the two end tails to the middle region, wherein the releasable junction is removable when the releasing suture is pulled out of the suture.

16. The surgical construct of claim 15, wherein pulling the releasing suture completely out of the suture removes the releasable junction and opens up the closed, flexible, continuous end loop with a fixed perimeter.

17. The surgical construct of claim 15, wherein the releasable junction is formed of a plurality of passes extending between the middle region and the one of the two end tails.

18. A surgical construct comprising:
a suture with a middle region and two end tails; and
a strand passed multiple times through the middle region and through one of the two end tails to form a closed, flexible, continuous end loop with a fixed perimeter and a releasable junction, and to connect the one of the two end tails to the middle region, wherein the strand passes through the other of the two end tails.

* * * * *